United States Patent [19]

Katsumoto

[11] 3,970,708

[45] July 20, 1976

[54] PROCESS FOR REMOVING ALUMINUM PHENOXIDE CATALYST FROM PHENOL ALKYLATION PRODUCTS

[75] Inventor: Kiyoshi Katsumoto, El Cerrito, Calif.

[73] Assignee: Chevron Research Company, San Francisco, Calif.

[22] Filed: Dec. 26, 1974

[21] Appl. No.: 536,500

[52] U.S. Cl. .................... 260/624 C; 260/621 A; 252/431 R
[51] Int. Cl.$^2$ .......................................... C07C 39/06
[58] Field of Search ........ 260/624 R, 624 C, 624 A, 260/621 B, 621 A, 621 R; 252/431, 624 A

[56] References Cited
UNITED STATES PATENTS

| | | | |
|---|---|---|---|
| 2,831,898 | 4/1958 | Ecke et al. ................... | 260/624 C |
| 3,652,685 | 3/1972 | Geddes ......................... | 260/624 C |

*Primary Examiner*—James O. Thomaas Jr.
*Assistant Examiner*—W. B. Lone
*Attorney, Agent, or Firm*—G. F. Magdeburger; John Stoner, Jr.

[57] ABSTRACT

In a process for the production of alkyl phenols by alkylating phenols with olefins in the presence of an aluminum phenoxide catalyst, removal of spent catalyst by adding water to reaction mixture and filtering is hastened by the presence of a neutral monomeric inorganic salt of polyvalent anion and an alkali metal, alkaline earth metal or ammonium cation.

3 Claims, No Drawings

PROCESS FOR REMOVING ALUMINUM PHENOXIDE CATALYST FROM PHENOL ALKYLATION PRODUCTS

BACKGROUND OF THE INVENTION

This invention is concerned with an improved method for removing aluminum hydroxide from an aluminum alkylphenol reaction mixture.

DESCRIPTION OF THE PRIOR ART

Alkylphenols have been prepared by the reaction of olefins with aluminum phenoxide. This method produces products having a very high proportion of ortho alkyl materials. After completion of the reaction, a difficulty in separating the aluminum which is produced arises. U.S. Pat. No. 3,652,685 teaches a method for separating the spent aluminum and the alkylphenol. The method involves adding a critical amount of water, preferably about 3 to 6 mols per gram atom of aluminum present in the reaction product, followed by filtering the aluminum, presumably in the form of a hydrated aluminum hydroxide, from the mixture by conventional filtration techniques.

SUMMARY OF THE INVENTION

It has now been found that the filtration rate of aluminum from an alkylphenol reaction mixture can be greatly increased by the addition of certain inorganic salts to the reaction mixture prior to filtration.

The salts which may be used are neutral monomeric inorganic salts of a polyvalent anion and an alkali metal, alkaline earth metal or ammonium cation.

Examples of suitable salts are sodium sulfate, sodium phosphate, sodium calcium phosphate, ammonium sulfate, and ammonium carbonate. A particularly useful material is diammonium hydrogen phosphate.

The salt may be added to the mixture any time before filtration; however, to assure adequate mixing, it is preferably mixed with the water and added.

The amount of salt employed will generally be in the range 0.05 to 5.0 parts by weight relative to the aluminum present in the mixture. The preferred range is from about 0.5 to 1 part.

The reaction product mixture may contain from about 20 to 90 percent by weight of alkylphenol, from 10 to 80 percent of unreacted phenol and from about 0.1 to 4.0 percent of aluminum in the form of phenoxide. More usually it will contain from about 30 to 80 percent by weight of alkylphenol, from 20 to 70 percent of unreacted phenol and from about 0.5 to 2.0 percent of aluminum. Some unreacted olefin may be present as well as inert diluents such as higher n-paraffin.

The alkylation reaction is accomplished by contacting the olefin, phenol and catalyst at suitable temperature. The olefin may be added neat, but often it is diluted with a hydrocarbon diluent. Suitable diluents include branched and normal paraffins of 12 to 24 carbon atoms. Often, since the olefin will be derived by dehydrogenation of a paraffin or dehydrohalogenation of a halogenated paraffin, the diluent will be the paraffin corresponding to the olefin employed. Thus, for example, when octadecene is used the diluent will comprise primarily octadecane. The diluent, of course, will not enter the reaction and will be present in the reaction product mixture in amounts up to about 24 parts per part of phenol, more usually from about 3 to 20 parts.

Water is added to hydrolyze the aluminum phenoxide usually immediately after alkylation at a temperature of from about 0° to 230°C, preferably 75° to 180°C, and the mixture is agitated by appropriate means for a sufficient time, e.g., 1 to 120 minutes, preferably 5 to 90 minutes, to allow intimate contact of the water with the mixture. The salt is preferably dissolved in the water before its addition to the mixture, although it may be added at any time prior to filtration.

After removal of the catalyst by filtration the phenol and diluent may be removed by distillation, preferably under vacuum. Further distillation will allow obtaining a heart cut of the desired alkylphenol, the purity of which is assured by this process and is quite important in detergent preparation. The maintenance of good color of detergent formulations is necessary, and it has been found that the present method produces material which upon sulfonation yield products of good color.

Both steps, i.e., water addition and precipitate separation, are essential in the present invention. If the critical amount of water is added, but the precipitated catalyst decomposition product is not removed before fractional distillation, some degradation will occur during the distillation thereby giving an impure heart cut alkylphenol. If water is not added, and the reaction product is simply filtered, some catalyst material may be removed but most of it will still be present and decomposition will occur during the subsequent distillation.

EXAMPLES

The invention is illustrated by the following examples, which are but illustrative and nonlimiting.

Example 1 — Alkylation of phenol with $C_{17}$–$C_{20}$ linear monoolefin in the presence of aluminum phenoxide catalyst The olefin starting material had a boiling range of 162°–280°C/10 mm Hg and a mass distribution of $C_{17}$, 25%; $C_{18}$, 31%; $C_{19}$, 27%; $C_{20}$, 18%. It contained 1.4% alpha-olefin, 26% cis- and trans-2-olefin, and 73% 3- and higher internal olefins. It also contained about 8% n-paraffin (mostly $C_{19}$ and $C_{20}$).

An aluminum phenoxide catalyst was prepared by dissolving 45 grams of aluminum in 2195 grams of phenol at 157°C. Then 2195 grams of phenol and 4086 grams of the olefin starting material were mixed with the catalyst containing phenol. The resulting mixture was heated for 2 hours at 232°–250°C in a stirred 5-gallon autoclave under a nitrogen atmosphere.

Example 2 — Filtration with Salt Addition

A series of filtrations was accomplished using the general method of Example 1 with water addition before filtration. Various salts were added, and filtration times were determined for each sample.

The following Table shows results obtained in filtering various samples obtained in a manner similar to Example 1. Filtrations are indicated in time required to filter 300 cc. The alkylphenol employed had an alkyl carbon content of 17–19 carbon atoms. The time and temperature for catalyst hydrolysis, weight percent water used, type and amount of additive (salt) employed, and filtration temperature are set forth in Table.

TABLE

EFFECT OF SALT ADDITION UPON FILTRATION TIME OF LINEAR ALKYLPHENOL

| No. | Additive Type | Wt. % | Hydrolysis Temp. °C. | Time Min. | Water Added Wt.% | Filtration Temp. °C. | Time Min. |
|---|---|---|---|---|---|---|---|
| 2-1 | No additive | — | 165 | 5 | 1 | 165 | 58 |
| 2-2 | $Na_2(O_2CCHOH)_2 \cdot 2H_2O$ | 0.2 | 165 | 5 | 1 | 160 | 11 |
| 2-3 | $Na_2SiO_3 \cdot 9H_2O$ | 0.2 | 165 | 5 | 1 | 165 | 14 |
| 2-4 | $Na_2SO_4$ | 0.2 | 165 | 5 | 1 | 170 | 8.5 |
| 2-5 | Clay | 2 | 165 | 5 | 2 | 167 | 62 |
| 2-6 | $Na_2SiO_3 \cdot 9H_2O$ | 1 | 300 | 60 | 1 | 152 | 11.3 |
| 2-7 | — | | 300 | 60 | 2 | 150 | 7.5 |
| 2-8 | $(NH_4)_2HPO_4$ | 0.2 | 300 | 60 | 1 | 158 | 2.3 |
| 2-9 | $(NH_4)_2HPO_4$ | 0.4 | 300 | 60 | 2 | 156 | 1.5 |
| 2-10 | $(NH_4)_2HPO_4$ | 0.2 | 200 | 60 | 1 | 155 | 2.2 |
| 2-11 | $(NH_4)_2HPO_4$ | 0.4 | 200 | 60 | 2 | 157 | 2.0 |

These data show that the addition of the salts significantly decreases the time required for filtration of the catalyst residue from the alkylation product.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:

1. In a process for removing aluminum phenoxide catalyst from ortho-alkylphenols produced by the reaction of phenol with an olefin in the presence of aluminum phenoxide catalyst wherein the catalyst is removed at the termination of the reaction by the addition of from 3 to 12 mols of water per atom of aluminum to the reaction product at a temperature of from about 0° to 230°C to form a precipitate followed by filtration of the precipitate from the reaction product mixture the improvement which comprises adding from about 0.05 to 5.0 parts of a neutral monomeric inorganic salt of a polyvalent anion and an alkali metal or ammonium cation selected from the group consisting of sulfates, silicates, phosphates, and carbonates to said mixture prior to filtration.

2. The process of claim 1 wherein said inorganic salt is present in the amount from about 0.5 to 1 part relative to the aluminum in the product.

3. The process of claim 1 in which the salt is ammonium phosphate.

* * * * *